United States Patent
Kubo (10) Patent No.: US 7,029,448 B2
(45) Date of Patent: Apr. 18, 2006

(54) ELECTRONIC HEMOMANOMETER AND BLOOD PRESSURE MEASURING METHOD OF ELECTRONIC HEMOMANOMETER

(75) Inventor: Takeshi Kubo, Kyoto (JP)

(73) Assignee: Omron Corporation, Kyoto (JP)

( * ) Notice: Subject to any disclaimer, the term of this patent is extended or adjusted under 35 U.S.C. 154(b) by 0 days.

(21) Appl. No.: 10/509,019

(22) PCT Filed: Mar. 18, 2003

(86) PCT No.: PCT/JP03/03287

§ 371 (c)(1),
(2), (4) Date: Sep. 27, 2004

(87) PCT Pub. No.: WO03/082100

PCT Pub. Date: Sep. 10, 2003

(65) Prior Publication Data

US 2005/0119578 A1   Jun. 2, 2005

(30) Foreign Application Priority Data

Mar. 28, 2002   (JP) ............................. 2002-091989

(51) Int. Cl.
*A61B 5/02* (2006.01)
(52) U.S. Cl. ...................................... 600/490; 600/500
(58) Field of Classification Search ........ 600/490–499, 600/500–504
See application file for complete search history.

(56) References Cited

U.S. PATENT DOCUMENTS

| | | | |
|---|---|---|---|
| 4,830,019 A | | 5/1989 | Shirasaki et al. |
| 4,944,305 A | * | 7/1990 | Takatsu et al. ............. 600/496 |
| 5,836,887 A | * | 11/1998 | Oka et al. ................... 600/494 |
| 5,868,679 A | * | 2/1999 | Miyazaki .................... 600/494 |
| 6,589,186 B1 | * | 7/2003 | Nishibayashi ............... 600/494 |

FOREIGN PATENT DOCUMENTS

| | | |
|---|---|---|
| JP | 61-253040 | 11/1986 |
| JP | 62-292139 | 12/1987 |
| JP | 63-286135 | 11/1988 |
| JP | 4-180728 | 6/1992 |
| JP | 5-58335 | 8/1993 |

OTHER PUBLICATIONS

"Idea to measure diastolic arterial pressure by volume oscillometric method in human fingers", Medical & Biological Engineering & Computing, Sep. 1986, pp. 549-554.

* cited by examiner

Primary Examiner—Robert L. Nasser
Assistant Examiner—Navin Natnithithadha
(74) Attorney, Agent, or Firm—Morrison & Foerster LLP (57) ABSTRACT

Oscillometry or another method is employed to initially determine a mean blood pressure and a diastolic blood pressure. There is a similarity between an intra-arterial pressure waveform exactly representing blood pressure and a pulse wave form generated when a cuff occludes a site to be measured. This similarity is utilized to obtain blood pressure. More specifically, the cuff occludes a site to be measured, while a pulse wave is detected. From the detected pulse wave's maximum amplitude an estimated mean arterial pressure is obtained. The obtained estimated mean arterial pressure and the pulse wave's minimum value are regarded as a mean blood pressure and a diastolic blood pressure, respectively. From the pulse wave's maximum value a systolic blood pressure is obtained by an arithmetic operation.

12 Claims, 10 Drawing Sheets

ELECTRONIC HEMOMANOMETER AND BLOOD PRESSURE MEASURING METHOD OF ELECTRONIC HEMOMANOMETER

TECHNICAL FIELD

The present invention relates generally to electronic blood pressure monitors and methods employing the same to calculate blood pressure and particularly to electronic blood pressure monitors that do not occlude a site to be measured with a pressure of no less than a systolic blood pressure so that the systolic blood pressure can be calculated with precision and methods employing the same to calculate blood pressure.

BACKGROUND ART

A blood pressure measuring instrument having interest in the present invention is disclosed for example in Japanese Patent Laying-Open No. 4-180728. For example as described in this document a similarity between a cuff pressure waveform and an arterial pressure waveform is utilized and a cuff pressure pulse waveform's areal barycenter position is correlated to a cuff pressure for a maximum amplitude to determine a systolic blood pressure from a diastolic blood pressure.

Mr. Shimazu discloses in an article entitled "Idea to measure diastolic arterial pressure by volume oscillometric method in human fingers," Medical & Biological Engineering & Computing, Sept. 1986, pp. 549–554 employing volume oscillograph to determine a systolic blood pressure and a mean blood pressure and therefrom determining a diastolic blood pressure.

Furthermore, Japanese Patent Publication No. 5-58335 (Japanese Patent Laying-Open No. 62-292139) discloses utilizing a pressure lower than a systolic blood pressure to obtain a systolic blood pressure by extrapolation.

Japanese Patent Laying-Open No. 4-180728 discloses a method of measurement utilizing a similitude between a cuff pressure pulse wave and an arterial pressure waveform. This method, however, correlates the cuff pressure pulse waveform's areal barycenter position to a cuff pressure exerted when a maximum amplitude appears, and its measurement theory is arguable in validity.

Furthermore, as described in Mr. Shimazu's article, a similitude between a volume pulse waveform and a blood pressure waveform detected via a photoelectric sensor at a finger tip to be measured is utilized to allow a systolic blood pressure to be determined with increased precision, and this requires exerting a cuff pressure to occlude a site to be measured to attain a pressure of no less than a systolic blood pressure.

Japanese Patent Publication No. 5-58335 (Japanese Patent Laying-Open No. 62-292139) discloses exerting a pressure lower than a systolic blood pressure for occlusion to determine a systolic blood pressure. This method, however, calculates the systolic blood pressure by an expression using an experimentally obtained, fixed constant, and thus suffers an error attributed to a variation attributed to a physiological difference between individual subjects.

DISCLOSURE OF THE INVENTION

The present invention has been made to overcome such disadvantageous as described above and contemplates an electronic blood pressure monitor capable of measuring a systolic blood pressure non-invasively with high precision and a method employing the same to calculate blood pressure.

The present electronic blood pressure monitor having a cuff attached on a subject and pressurized and depressurized to measure the subject's blood pressure, includes: a pulse wave detector detecting the subject's pulse wave as the cuff occludes the subject; a mean blood pressure estimator estimating the subject's mean blood pressure from the pulse wave detected by the pulse wave detection means; a diastolic blood pressure detector detecting the subject's diastolic blood pressure; and a systolic blood pressure calculator calculating the subject's systolic blood pressure from the estimated mean arterial pressure, the diastolic blood pressure detected and the pulse wave's waveform.

As the cuff occludes a subject the subject's pulse wave is detected and from the detected pulse wave the subject's mean blood pressure is estimated and the subject's diastolic blood pressure is also detected. The estimated mean arterial pressure, the detected diastolic blood pressure and the pulse wave's waveform are used to calculate the subject's systolic blood pressure as based on a similarity between pulse waveform and intra-arterial pressure waveform. The necessity of pressurization of no less than systolic blood pressure can be eliminated, and systolic blood pressure can still be measured invasively with high precision.

Preferably the pulse wave detector includes a waveform parameter calculator calculating a waveform parameter indicative of a feature of a waveform of a pulse wave detected, and the diastolic blood pressure detector includes a diastolic blood pressure calculator using the waveform parameter to calculate diastolic blood pressure. The mean blood pressure estimator employs the waveform parameter to determine a reference pressure point within any range of no more than a systolic blood pressure to no less than a diastolic blood pressure and with reference to the reference pressure point calculates estimated mean arterial pressure by using the waveform parameter correlated with an average value of intra-arterial pressure waveform. The systolic blood pressure calculator correlates the diastolic blood pressure and the estimated mean arterial pressure to the pulse waveform's maximum and average values and calculates a blood pressure corresponding to the pulse waveform's maximum value point to determine systolic blood pressure.

The electronic blood pressure monitor calculates an estimated mean arterial pressure with reference to a determined reference pressure by a pulse waveform parameter correlated to an average value of intra-arterial pressure waveform, and correlates diastolic blood pressure and the calculated, estimated mean arterial pressure to pulse waveform's maximum and average values to calculate a value corresponding to the pulse waveform's maximum value point. The calculated, resultant value can be determined as systolic blood pressure. The necessity of pressurization of no less than systolic blood pressure, and systolic blood pressure can still be measured non-invasively with high precision.

Preferably the blood pressure monitor further includes a waveform distortion corrector correcting the waveform parameter to cancel an error introduced by a distortion of a detected pulse wave relative to the intra-arterial waveform into systolic blood pressure calculated.

Distortion of a detected pulse waveform relative to an intra-arterial pressure waveform can be corrected to cancel an error introduced in systolic blood pressure calculated. An error in blood pressure calculation that is attributed to a difference between an intra-arterial pressure waveform and a detected pulse waveform can thus be reduced.

The difference between a detected pulse wave's waveform and an intra-arterial pressure waveform is attributed to individual pulse wave detection methods. Accordingly, methods of correction unique to the detection methods, respectively, are employed to correct distortion.

Correction of distortion in waveform is preferably obtained as based on a pulse waveform parameter representative of a relationship between intra-arterial pressure and vascular volume as the cuff occludes the subject, i.e., representative of arterial elasticity characteristic. Distortion introduced by a difference between individuals' arterial elasticity characteristics can be corrected. More precise measurement can be achieved.

Preferably the mean blood pressure estimator determines as the estimated mean arterial pressure a cuff pressure allowing a pulse wave amplitude to be maximized.

On the other hand, the mean blood pressure estimator may use an area of an apical portion of a pulse wave amplitude envelope in an arithmetic operation to determine estimated mean arterial pressure or may use a minutia of a waveform parameter indicative of stiffness in a vicinity of a pulse wave rising point to determine estimated mean arterial pressure.

More preferably the electronic blood pressure monitor further includes a flat-amplitude detector detecting whether there exists a cuff pressure range free of significant variation in pulse wave amplitude when the cuff pressure is changed, and when estimated mean arterial pressure is present within a cuff pressure range free of significant variation in pulse wave amplitude, systolic blood pressure is determined from one or both of estimated mean arterial pressure obtained by the mean blood pressure estimator.

Consequently when estimated mean arterial pressure is present within a cuff pressure range free of significant variation in pulse wave amplitude a more appropriate method can be used to estimate mean blood pressure.

More preferably, systolic blood pressure is calculated for each pulse wave of a plurality of pulses obtained during measurement and such systolic blood pressures thus obtained are averaged together to provide an ultimate systolic blood pressure.

More preferably, the electronic blood pressure monitor further includes a pulse wave average calculator calculating average values of a plurality of pulse waves, respectively, detected by the pulse wave detector, and the systolic blood pressure calculator calculates systolic blood pressures for the plurality of pulse waves, respectively, from the average values calculated by the pulse wave average calculator, and determines an average of these calculated systolic blood pressures as an ultimate systolic blood pressure. Resultant measurement can have increased reliability and also be more practical.

The systolic blood pressure calculator preferably calculates systolic blood pressure for each pulse waveform of a plurality of pulses obtained during measurement, classifies such results into a plurality of classes within a range of a cuff pressure being applied when a pulse wave is generated, and performs an operation weighting an average value of each class to determine a systolic blood pressure to be a result of the measurement. Thus measurement can provide a result further increased in reliability.

The electronic blood pressure monitor preferably further includes a blood pressure variation range display unit calculating a systolic blood pressure for each pulse wave of a plurality of pulses obtained during measurement, and displaying how a plurality of systolic blood pressures vary in value. Thus, systolic blood pressure can be calculated for each pulse waveform of a plurality of pulses obtained during measurement and the obtained systolic blood pressure values' variation can be represented numerically or diagrammatically. By confirming displayed item(s) the user can confirm respiratory blood pressure variation, variation attributed to arrhythmia, and the like.

The present invention in another aspect provides a blood pressure calculation method employing an electronic blood pressure monitor having a cuff attached on a subject and pressurized and depressurized in order to calculate the subject's blood pressure, including the steps of: detecting a pulse wave of the subject occluded by the cuff, estimating the subject's mean blood pressure from a pulse wave detected; detecting the subject's diastolic blood pressure; and calculating the subject's systolic blood pressure from an estimated mean arterial pressure, the detected diastolic blood pressure and the detected pulse wave's waveform.

An estimated mean arterial pressure, a detected diastolic blood pressure and a pulse wave's waveform can be used to calculate a systolic blood pressure. Systolic blood pressure can thus be measured non-invasively with high precision.

The step of detecting a pulse wave includes the step of calculating a waveform parameter indicative of a feature of a waveform of a pulse wave detected, and the step of calculating a diastolic blood pressure using the waveform parameter.

In the step of estimating a mean blood pressure the waveform parameter is used to determine a reference pressure point within any range of no more than a systolic blood pressure to no less than a diastolic blood pressure and calculates an estimated mean arterial pressure with reference to the reference pressure point by a waveform parameter correlated with an average of intra-arterial pressure waveform.

In the step of calculating a systolic blood pressure, the diastolic blood pressure and the estimated mean arterial pressure are correlated to the pulse waveform's minimum and average values and a blood pressure corresponding to the pulse waveform's maximum value point is calculated to determine systolic blood pressure.

The method further includes the step of correcting a distortion in waveform, correcting the waveform parameter to cancel an error introduced by a distortion of a detected pulse waveform relative to the intra-arterial pressure waveform into systolic blood pressure calculated.

BEST MODES FOR CARRYING OUT THE INVENTION

Hereinafter the present invention in embodiment will be described with reference to the drawings.

Figure 1:
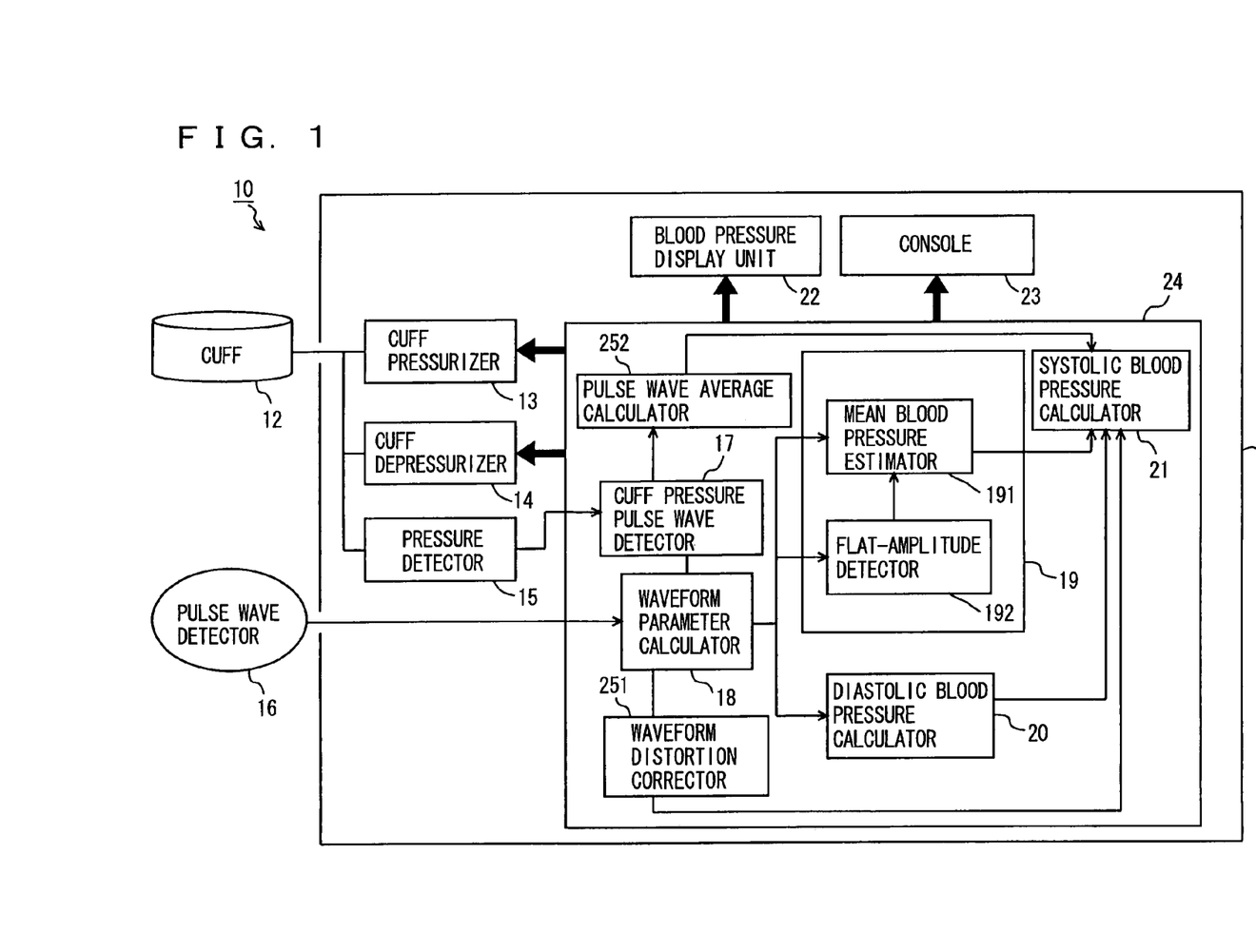
FIG. 1 is a block diagram showing a main portion of an electronic blood pressure monitor.

FIG. 1 is a block diagram showing a main portion of an electronic blood pressure monitor in accordance with the present invention. With reference to FIG. 1, an electronic blood pressure monitor 10 includes a body 11 of the blood pressure monitor, a cuff 12 attached to a subject on a site to be measured, and a pulse wave detector 16 detecting a pulse wave in the form of a signal when cuff 12 occludes the site to be measured. Body 11 includes a controller 24 generally controlling the blood pressure monitor, a cuff pressurizer 13 pressurizing cuff 12, a cuff depressurizer 14 depressurizing cuff 12, a pressure detector 15 detecting the cuff 12 internal pressure (hereinafter referred to as a "cuff pressure"), a blood pressure display unit 22 displaying measured blood pressure, and a console 23 operated to generally operate the blood pressure monitor.

Controller 24 includes a cuff pressure pulse wave detector 17 connected to pressure detector 15, a pulse waveform parameter calculator 18 connected to pulse wave detector 16, a reference pressure determiner 19, a diastolic blood pressure calculator 20, a systolic blood pressure calculator 21, a waveform distortion corrector 251, and a pulse wave average calculator 252. Reference pressure determiner 19 includes a mean blood pressure estimator 191 using a pulse waveform parameter to estimate a subject's mean blood pressure, and a flat-amplitude detector 192 detecting a flat portion in amplitude of a pulse waveform.

Figure 2:
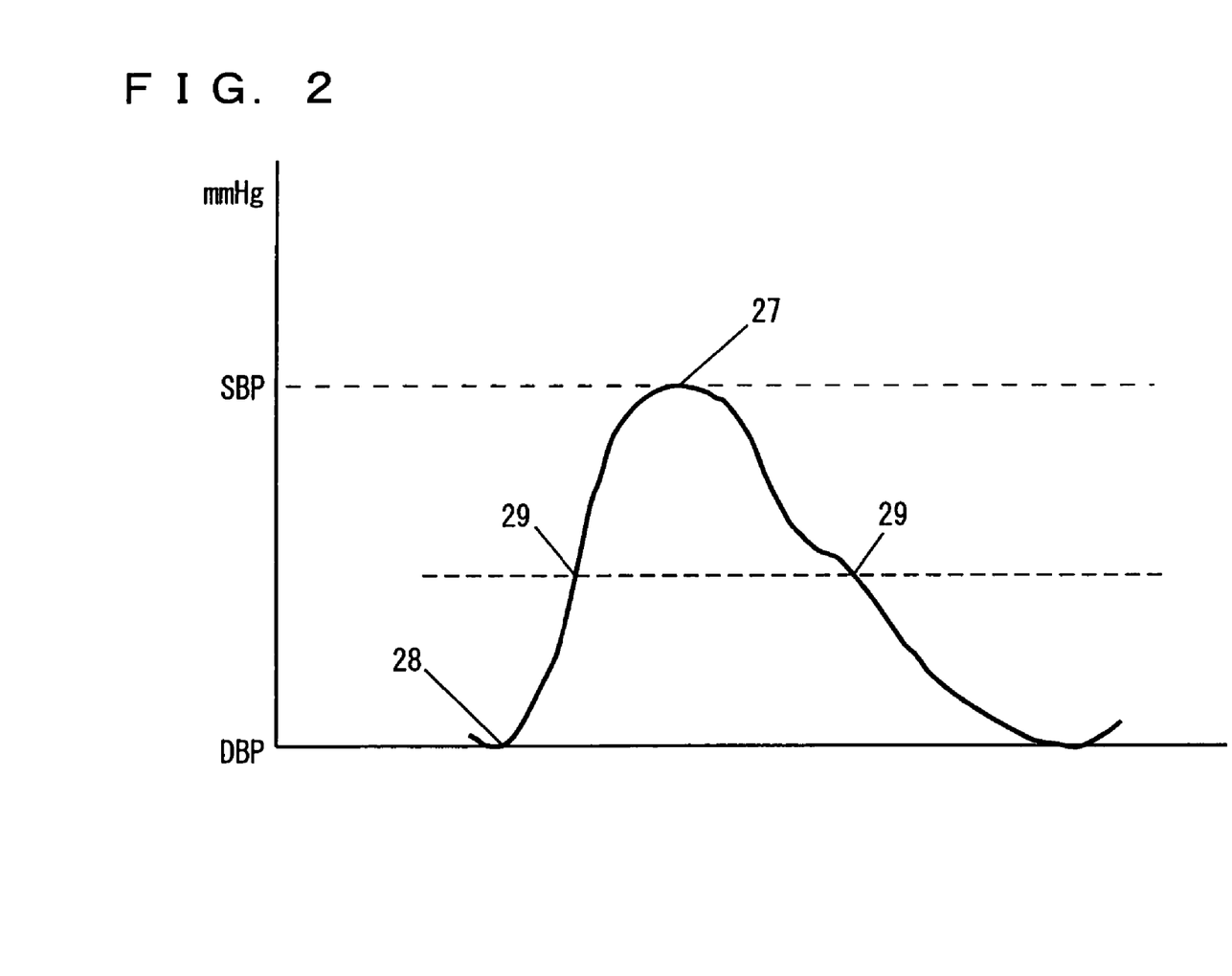
FIG. 2 is a view for illustrating a principle of detection of blood pressure when the present electronic blood pressure monitor is used.

In the present invention, measurement is done in accordance with a principle, as will now be described with reference to FIGS. 1 and 2. FIG. 2 shows a waveform of one cycle of a pulse wave when cuff 12 exerts pressure. The FIG. 2 pulse wave has characteristics of an amplitude Am and an average value Av, as will be described later. It is known that this pulse waveform is analogous to an intra-arterial pressure waveform. Accordingly from a waveform of a pulse wave detected for example by pulse wave detector 16 the pulse waveform's minimum value 28, average value 29 and maximum value 27 are obtained. Furthermore, some method described later is used to obtain the subject's mean blood pressure and minimum or diastolic blood pressure (DBP). Therefrom, the pulse waveform's minimum and average values are regarded as a diastolic blood pressure and a mean blood pressure, respectively, indicated by an intra-arterial pressure waveform and the value of an intra-arterial pressure waveform corresponding to the pulse waveform's maximum value 27 can be obtained through an arithmetic operation to obtain a maximum or systolic blood pressure (SBP).

Diastolic blood pressure can also be determined by oscillometry or other similar, typical blood pressure measurement methods without increasing a cuff pressure to be higher than a systolic blood pressure. Mean blood pressure is obtained at the location of a maximum amplitude of a pulse wave as cuff pressure is increased, as is known, and mean blood pressure may be obtained as such.

In blood pressure measurement a systolic blood pressure can be obtained without exerting no less than a prescribed pressure. The subject can be liberated from pain as conventional in blood pressure measurement.

Electronic blood pressure monitor 10 operates to determine a blood pressure in a procedure, as will now be described hereinafter with reference to the flow chart shown in FIG. 3.

Figure 3:
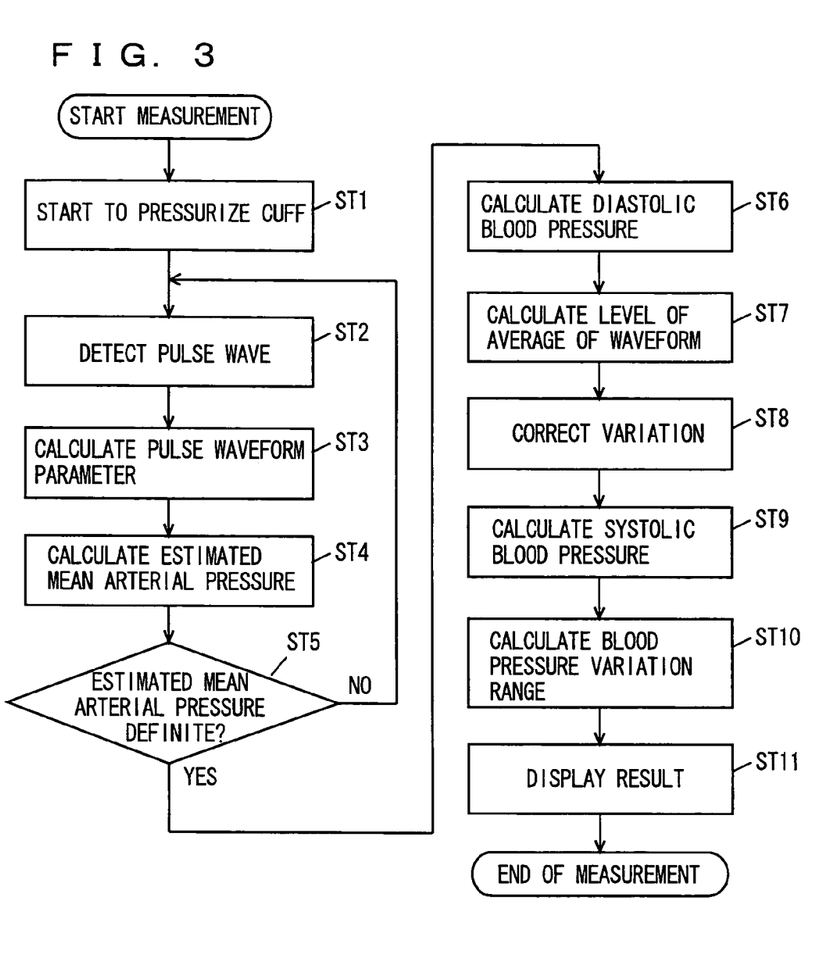
FIG. 3 is a flow chart representing a procedure of measurement using the electronic blood pressure monitor.

With reference to FIG. 3, a user presses a switch (not shown) of console 23 to start a measurement, when cuff pressurizer 13 pressurizes cuff 12 attached on a site to be measured.

The measurement can be done as pressure exerted is gradually increased similarly as when a conventional blood pressure monitor is used, or the measurement can be done as a prescribed pressure previously exerted is gradually reduced. In the following embodiment, the measurement is done as pressure exerted is increased, although the pressure may be increased or decreased, by any method.

When the measurement starts, cuff 12 is gradually pressurized (step (ST) 1) and pulse wave detector 16 detects a pulse wave generated at the site to be measured occluded by cuff 12 (ST2).

Pulse wave detector 16 may herein detect: a volume pulse wave via a photoelectric sensor; an impedance pulse wave, detecting a living body's electric impedance resulting from a variation of a blood stream attributed to pulsation; a variation in pressure as a pressure sensor is pressed on an artery; or the like.

Furthermore, other than the above, a small variation in pulsation that is superimposed on a cuff pressure detected by cuff 12 is detected as a cuff pressure pulse wave. In the present embodiment this cuff pressure pulse wave is used for description. A cuff pressure pulse wave is superimposed on a pressure signal indicating a cuff pressure detected by pressure detector 15 and when the cuff pressure pulse wave is used it is not necessary that pulse wave detector 16 detect other different type of pulse wave. This can advantageously simplify device and the electronic blood pressure monitor can inexpensively be configured. Hereinafter, a cuff pressure pulse wave will simply be referred to as a pulse wave.

Cuff pressure pulse wave detector 17 detects a signal which is in turn transmitted to waveform parameter calculator 18 calculating a waveform parameter representing an amount of a feature in waveform of a pulse wave (ST3).

The waveform parameter calculated is an amplitude Am representing a height of a pulse wave, an average value Aav representing an average of an area provided by a waveform of the pulse wave, and the like.

Figure 4:
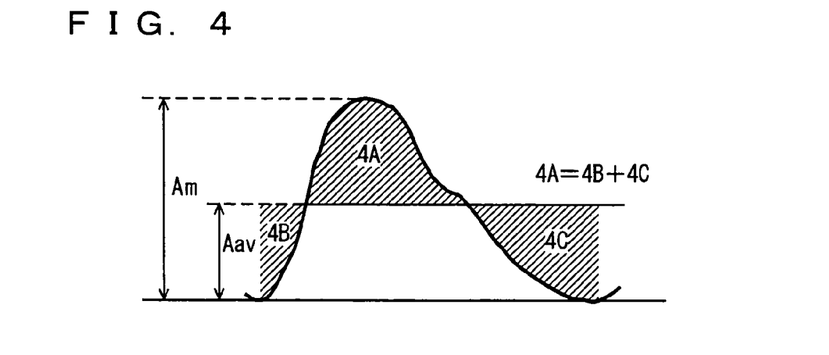
FIG. 4 represents pulse waveform's average value.

FIG. 4 represents these parameters. With reference to the figure, when a pulse waveform is cut at an area average indicated by average value Aav an upper area 4A is determined to be equal to a lower area 4B+4C. A waveform parameter is calculated as cuff 12 is continuously pressurized and whenever cuff pressure pulse wave detector 17 detects a pulse wave. Then, reference pressure determiner 19 obtains an estimated mean pressure (ST4).

Figure 5:
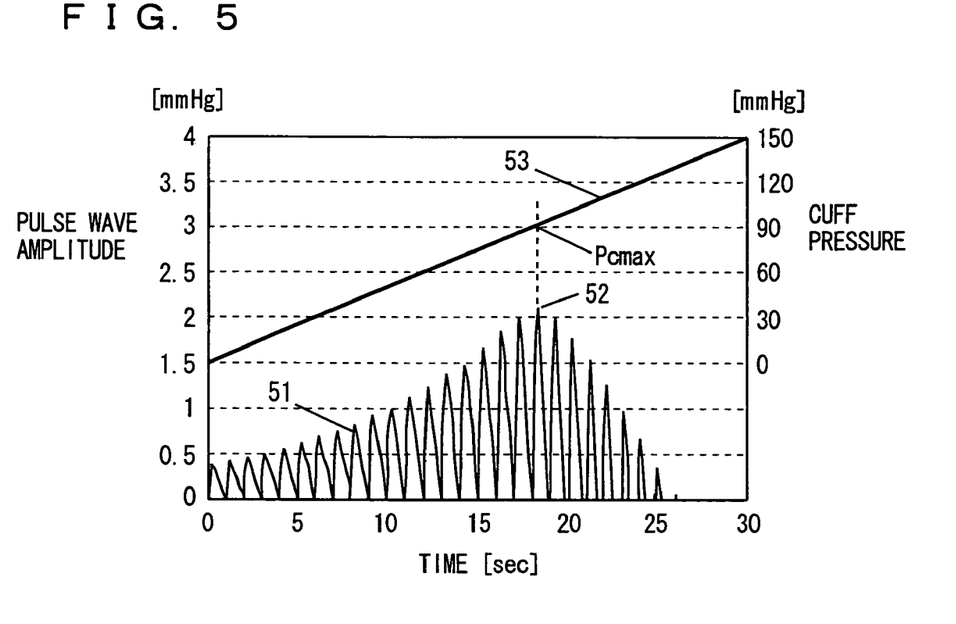
FIG. 5 represents a pulse waveform generated as a cuff is pressurized.

FIG. 5 shows a pulse wave 51 generated as time elapses while cuff 12 is increasingly pressurized. As shown in the figure, as a cuff pressure 53 is gradually increased there exists a point 52 allowing pulse wave 51 to be maximized in amplitude. When point 52 allowing pulse wave amplitude Am to be maximized (or peak) is indicated, cuff pressure detector 15 detects a cuff pressure Pcmax, which serves as an estimated mean arterial pressure.

Figure 6:
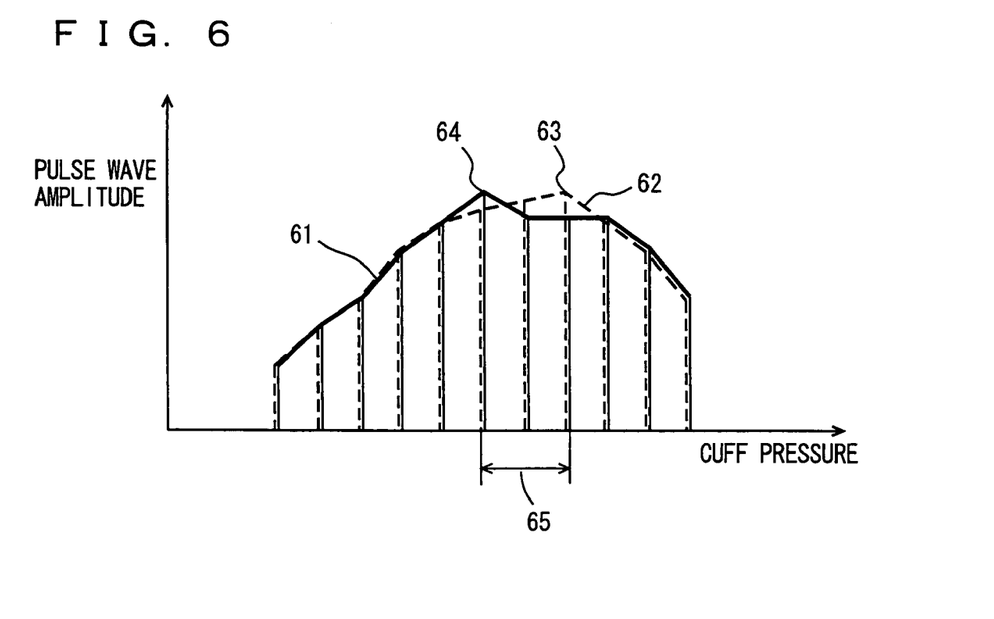
FIG. 6 represents a trapezoidal pulse waveform envelope.

FIG. 6 represents a relationship between a cuff pressure and a pulse wave amplitude envelope (a line indicating a variation in amplitude of a plurality of pulse waves (a line connecting maximum values in amplitude of the plurality of pulse waves, respectively)). Normally, as shown in FIG. 5, as cuff pressure 53 increases, pulse wave 51 increases in amplitude, and once it has passed its peak it decreases in amplitude. As such, maximum amplitude point 52 can be readily determined.

This, however, is not always the case. For example, a subject with advanced arteriosclerosis can provide a trapezoidal pulse wave amplitude envelope 61 as indicated in FIG. 6 by a solid line. This is because the subject has an artery impaired in elasticity and thus hard to expand to exceed a certain volume and if the cuff pressure varies relative to the intra-arterial pressure the artery's volume varies in a small amount. For a sufficiently elastic artery, a cuff pressure lower relative to an intra-arterial pressure should allow the artery to expand in volume to provide a pulse wave amplitude envelope 62 having a waveform indicated by a broken line. For trapezoidal envelope 61, if for example blood pressure varies introducing a small pulse wave amplitude variation factor then as shown in FIG. 6 a true maximum amplitude point 63 would be offset to a completely different maximum amplitude point 64. Between maximum amplitude points 63 and 64 there is detected a cuff pressure difference or error 65, which serves as a factor introducing a large error into a subsequent, systolic blood pressure calculation.

Figures 7A, 7B:
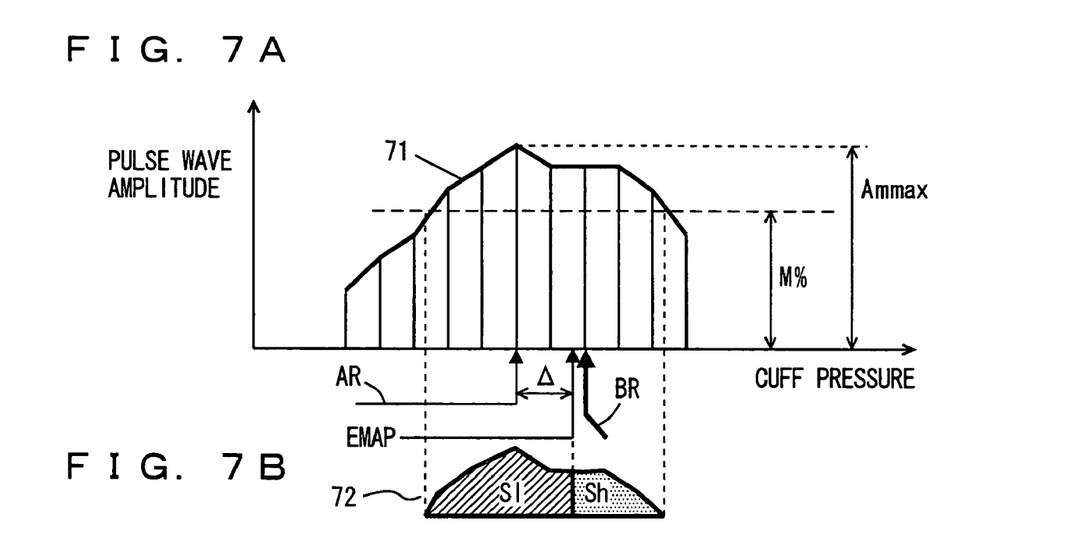
FIGS. 7A and 7B illustrate a procedure employed to calculate an estimated mean arterial pressure for a trapezoidal pulse wave envelope.

FIG. 7A represents a pulse wave envelope 71 and FIG. 7B represents an upper portion thereof alone cut 72 therefrom and shown in correlation therewith. After pulse wave of a maximum amplitude Ammax is detected, cuff 12 is increasingly pressurized until a pulse wave amplitude below a prescribed ratio M% of maximum amplitude Ammax is detected. The detected pulse wave amplitude is correlated in a graph to the cuff pressure applied when the pulse wave is generated. A pulse wave amplitude envelope indicated in FIG. 7B by cut portion 72 can thus be obtained. Pulse wave envelope 71 is cut at a level in amplitude of the prescribed ratio M% of maximum amplitude Ammax into upper and lower portions and when only the upper portion of envelope 71 is shown it presents a profile as indicated by cut portion 72. The cut portion 72 profile provides an area, which is divided at a cuff pressure corresponding to a prescribed ratio of Sl:Sh. This cuff pressure will be an estimated mean arterial pressure (EMAP). When in FIG. 7A a cuff pressure corresponding to a maximum amplitude value, as indicated by an arrow AR, is a mean blood pressure, error 65 from a true mean blood pressure, as indicated by an arrow BR, can be overcome by Δ, as shown in FIG. 7A. Ratio M% and area ratio Sl:Sh can be determined from data of envelope 71 of a large number of pulse waves to minimize error 65. As a result if a waveform varies, as shown in FIG. 6, estimated mean arterial pressure EMAP can nonetheless be prevented from significantly being offset from the true mean blood pressure indicated by arrow BR.

Figure 8:
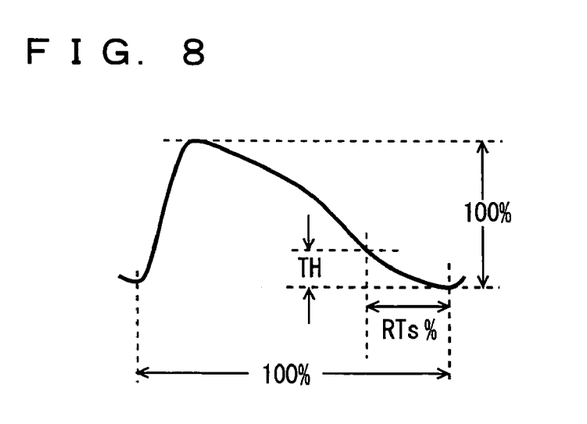
FIG. 8 is a view for illustrating a procedure employed to obtain a parameter representative of steepness observed before and after a pulse wave rises.
Figure 9:
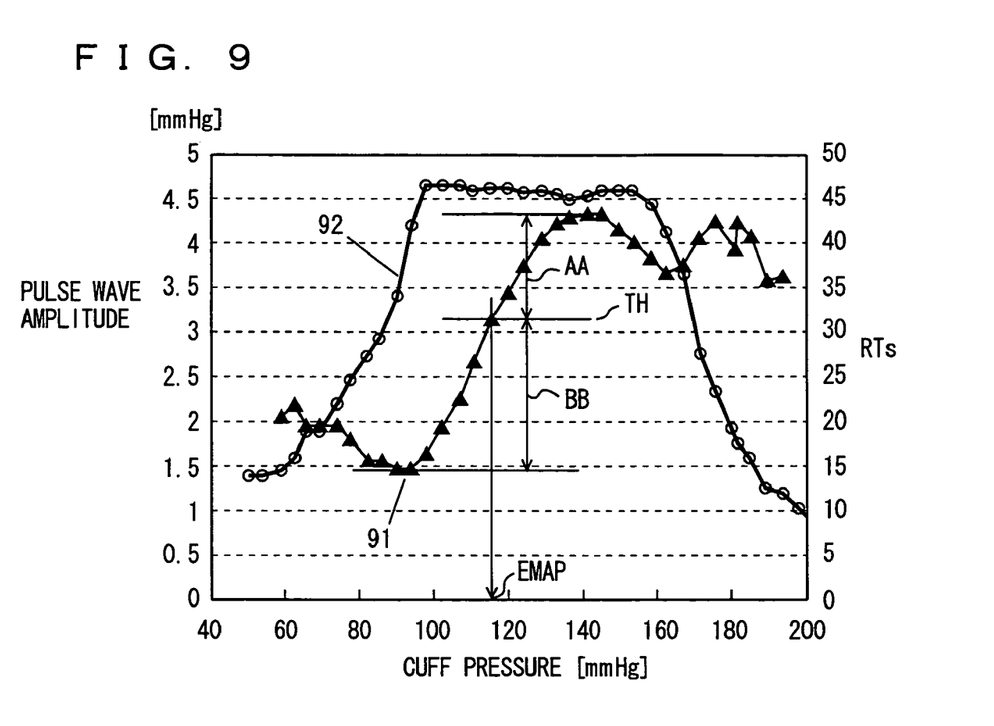
FIG. 9 shows how a parameter representative of steepness observed before and after a pulse wave rises, varies.

A true rough maximum amplitude point can also be obtained by a different method, as will be described hereinafter. Estimated mean arterial pressure EMAP is calculated with consideration given to a parameter RTs representative of steepness observed before and after a pulse wave rises. FIG. 8 shows a variation in a pulse wave. With reference to the figure, a ratio (%), relative to a period of a pulse wave, of a time that elapses after a threshold TH corresponding to approximately 10% relative to the pulse wave's amplitude is crossed and before the pulse wave subsequently rises, is set as parameter RTs representative of steepness and calculated by waveform parameter calculator 18. Parameter RTs varies as indicated in FIG. 9, as plotted with triangles, forming a curve 91, whenever a pulse wave is generated as the cuff pressure is gradually increased. In FIG. 9, circles plot a curve indicating a pulse wave amplitude envelope 92. Parameter RTs indicated by curve 91 is minimized in the vicinity of a diastolic blood pressure and as the cuff pressure is increased the parameter gradually increases and is maximized before a systolic blood pressure is reached. The minimum through maximum values form a range which is divided by a prescribed ratio of AA:BB or threshold TH, which determines a cuff pressure (in the figure, a value indicated by EMAP) corresponding to estimated mean arterial pressure EMAP.

A mean blood pressure thus obtained allows a more accurate systolic blood pressure calculation.

Figure 10:
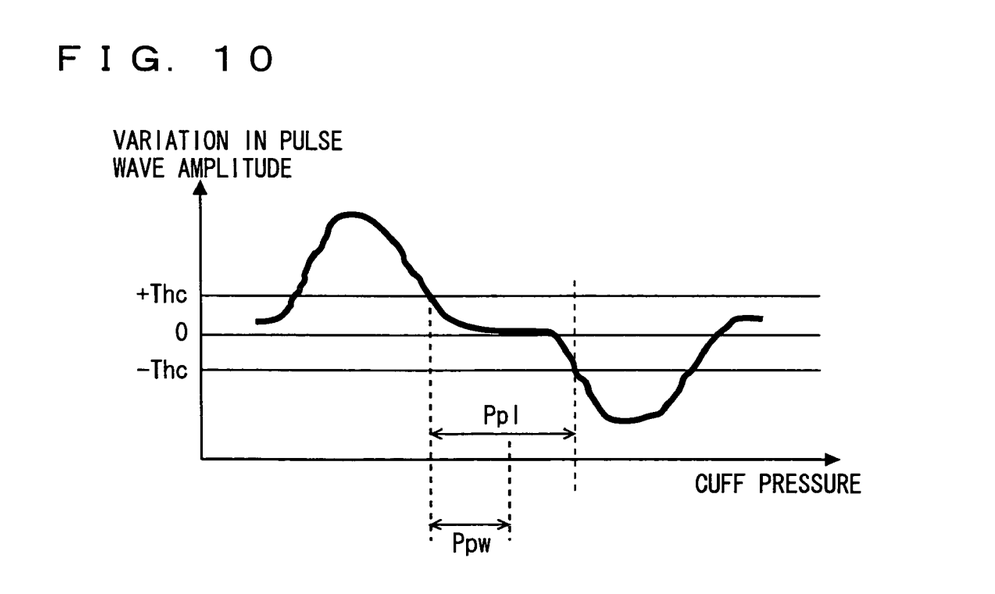
FIG. 10 represents a relationship between a cuff pressure and an amount of variation in pulse wave amplitude.

Estimated mean arterial pressure can also be calculated in a further exemplary variation, as will be described hereinafter. Herein, a detector 192 is used to detect a flat portion of an amplitude. With reference to FIG. 10, detector 192 calculates variation in amplitude successively whenever a pulse wave is detected. When detector 192 detects that a predetermined number of pulse waves successively enter a prescribed range±The thresholded used to determine whether a variation is a small variation or not or that while a pulse wave has an amplitude with a variation falling within range±The the current cuff pressure has variation Ppl exceeding a prescribed pressure range Ppw (a pressure range for decision), detector 192 determines that a trapezoidal pulse wave amplitude envelope is formed.

Thus in this example when detector 192 detecting that for a trapezoidal apex, amplitude has a significantly small variation detects that a pulse wave envelope is a trapezoidal, a different method can be used to estimate a mean blood pressure.

Thus at ST4 an estimated mean arterial pressure is obtained, and referring back to FIG. 3, ST5 is performed to determine whether the estimated mean arterial pressure value is definite. If not (NO at ST5), cuff 12 continues to increasingly exert pressure to detect an additional pulse wave (Return to ST2).

When an estimated mean arterial pressure is definite, diastolic blood pressure calculator 20 calculates a diastolic blood pressure (ST6) by conventional oscillometry from a pulse wave amplitude envelope obtained through the process to ST5. By this oscillometry, when a mean blood pressure is obtained a diastolic blood pressure is obtained. Furthermore, parameter RTs can also be used for decision. In the present embodiment a diastolic blood pressure is calculated by any method. It is not limited to any particular method.

Figure 11:
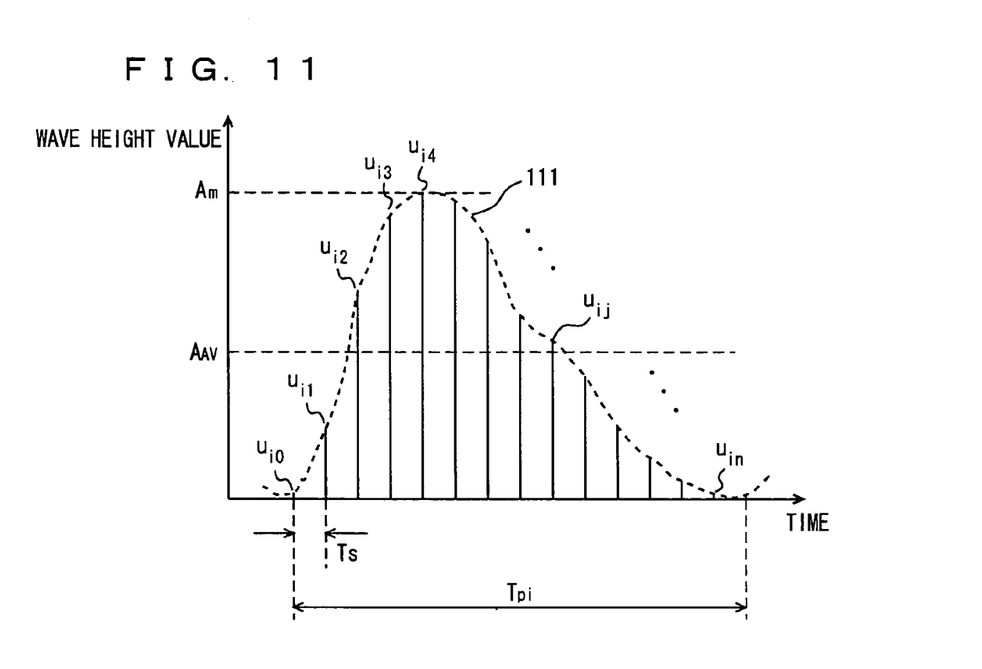
FIG. 11 is a diagram for illustrating a procedure employed to calculate a pulse wave average level.

At a subsequent step ST7, pulse wave average calculator 252 calculates an average value of a pulse waveform detected by cuff pressure pulse wave detector 17. FIG. 11 is a graph for illustrating a method of calculating an average value of a pulse waveform. A pulse waveform 111 is indicated in FIG. 11 by a broken line. An average value can be calculated for any pulse waveform 111 detected at cuff pressure of no more than estimated mean arterial pressure.

Basically, an average value can be calculated for a single pulse waveform and therefrom a systolic blood pressure can be calculated. On the other hand, a plurality of pulse waveforms may have their respective average values calculated and from the average values their respective systolic blood pressures may be calculated and averaged together to provide an ultimate systolic blood pressure. This allows measurement to provide a result enhanced in stability and is also practical. Thus in the present embodiment any pulse waveforms detected at cuff pressure lower than estimated mean arterial pressure have their average values calculated.

Pulse waveform 111 indicates a digital signal sampled for each cycle Ts, and a pulse wave has an average value calculated as follows:

In FIG. 11, sampling cycle Ts is employed to sample a pulse of one cycle to provide a digital signal indicating a value Uij, wherein j=0, 1, 2, 3, . . . , n, and the pulse waveform's maximum value Am is also shown. As based on one cycle of the pulse wave, or a time Tpi, a single pulse of the pulse waveform has an average value $A_{AV}$, as represented by the following equation (1):

$$A_{AV} = \sum_{j=0}^{n} u_{ij} \cdot \frac{T_S}{T_{pi}}. \tag{1}$$

When average value $A_{Av}$ is completely calculated, waveform distortion corrector 251 corrects waveform (ST8). More specifically, corrector 251 corrects a difference between a detected pulse waveform and an intra-arterial pressure waveform as it should be. A blood pressure calculation error otherwise resulting from the error between the two waveforms can thus be reduced.

The difference (a distortion in waveform) between a detected pulse waveform and an intra-arterial pressure waveform is attributed to how a pulse waveform is detected. Typically, a pulse wave is non-invasively detected by a method employed in the aforementioned embodiment including: extracting a cuff pressure pulse wave, a pulse wave component superimposed on a cuff pressure; detecting by a photoelectric sensor or through electric impedance or the like a volume pulse wave, a variation in volume of a blood vessel that results from pulsation; detecting a waveform of a pressure pulse wave, a pressure wave transmitted through pulsation as a distortion gauge or a similar pressure sensor is pressed against on a subject at an upper portion of an artery; and the like.

When a pulse wave is detected by a different method, distortion in waveform is caused for a different reason. Accordingly for different methods of detecting a pulse wave different methods for correction unique thereto are required, respectively.

When cuff 12 occludes a site to be measured and the intra-arterial pressure or blood pressure is higher than the cuff pressure the arterial wall moves to expand and when the intra-arterial pressure is lower than the cuff pressure the arterial wall moves to occlude. In other words, a pulse wave is generated as an artery varies in volume. This rhythmic variation in volume is referred to as a volume pulse wave. An intra-arterial pressure periodically varies as a heart rhythmically pumps out blood, and this variation is indicated as a blood pressure waveform, i.e., an intra-arterial pressure waveform.

A pressure applied by cuff 12, or a cuff pressure Pc, and an intra-arterial pressure Pa has a difference, which is a pressure exerted to an arterial wall, and the pressure exerted to the arterial wall and an arterial volume V has a relationship known as the pressure area relation.

Although a volume pulse wave is generated as described by the pressure area relation, as described above, the relationship between a pressure exerted to an arterial wall and an arterial volume (hereinafter this relationship will be referred to as a "PV curve") varies with arterial elasticity. As such, the relationship varies for each subject. Furthermore, arterial elasticity varies as influenced by sympathetic and parasympathetic nervous systems. More specifically, when a subject is for example in an environment having a rapid difference in temperature or experiences mental stress, his/her arterial elasticity varies. This variation affects pulse waveform and the pulse waveform's average value $A_{AV}$ will accordingly vary. As a result a systolic blood pressure varies in value, which in turn causes a measurement error. As will be described hereinafter, preferably, arterial elasticity parameter is detected from a parameter of a pulse wave as measured to correct an error introduced in calculating a systolic blood pressure. An error attributed to a difference in arterial elasticity for each individual can be corrected. More precise measurement can thus be achieved.

At ST8, the step of correcting a variation in waveform, an effect of a variation in elasticity of a blood vessel on a systolic blood pressure value calculated, as described above, is reduced by using an arterial elasticity parameter determined by measuring a gradient of a pulse waveform.

Figure 12:
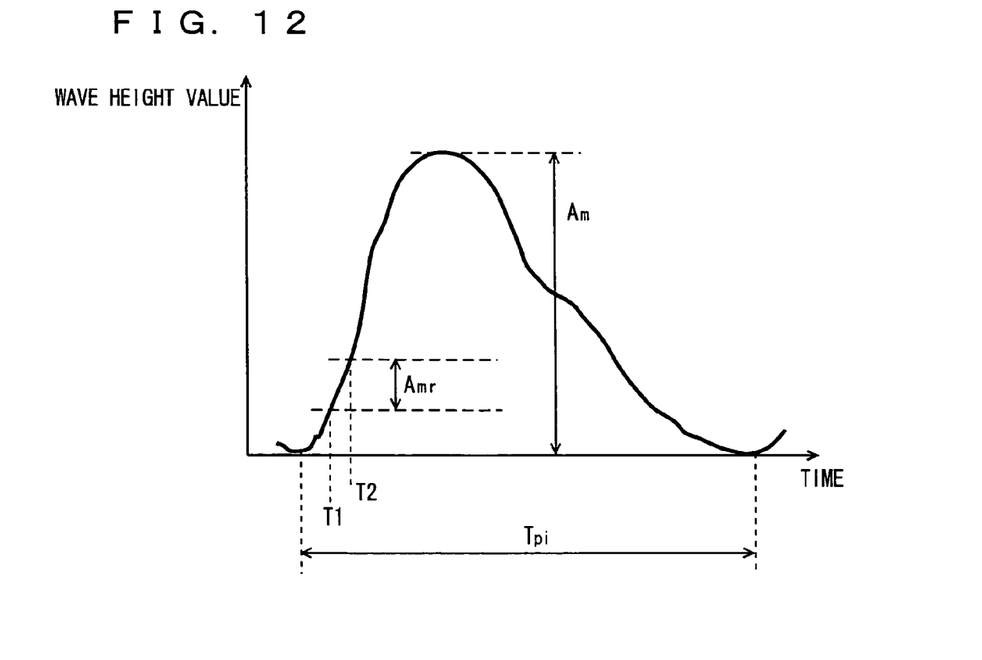
FIG. 12 is a diagram for illustrating a procedure employed to determine an arterial elasticity parameter.

A waveform is corrected by way of example, as will now be described hereinafter with reference to FIG. 12. With reference to the figure, a point at which a pulse wave rises is seen as a starting point and between prescribed two points of time T1 and T2 a pulse wave has an amplitude varying in an amount indicated by a gradient $\Delta Amr$ calculated by the following equation (2):

$$\Delta A_{mr} = \frac{A_{mr} \cdot T_{pi}}{A_m \cdot (T2 - T1)}. \tag{2}$$

Figure 13A:
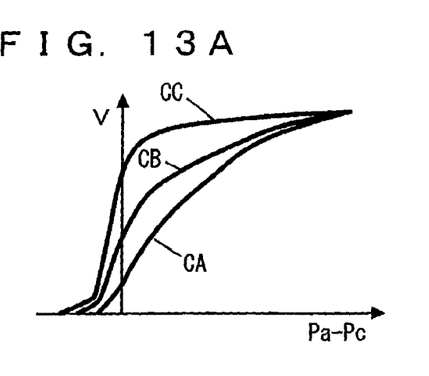
FIGS. 13A–13D represent a relationship between arterial stiffness and pulse waveform gradient.
Figure 13B:
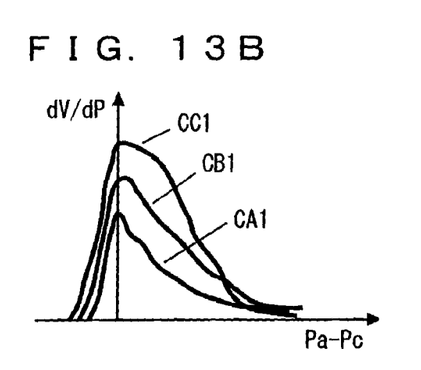

FIG. 13A represents how an arterial wall's pressure, i.e., intra-arterial pressure Pa minus pressure Pc externally exerted to the artery introduces variation in arterial volume, as represented by a PV curve. The PV curve has a gradient dV/dP, as shown in FIG. 13B.

Less elastic arteries are associated with PV curves having a tendency to vary from CA→CB→CC, with gradient dV/dP increasing, as indicated by CA1→CB1→CC1. Thus, gradient $\Delta Amr$ obtained from pulse waveform tends to increase for less elastic arteries.

Figure 13C:
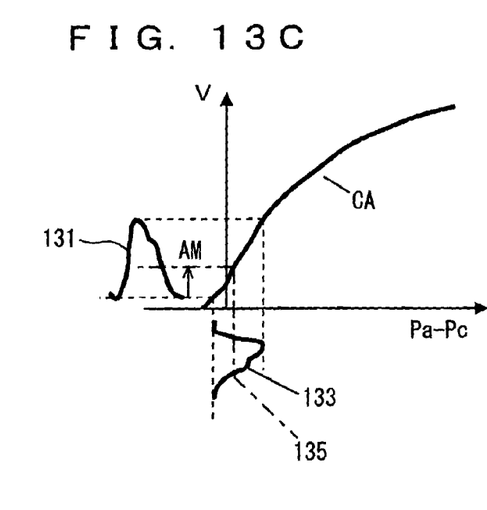
Figure 13D:
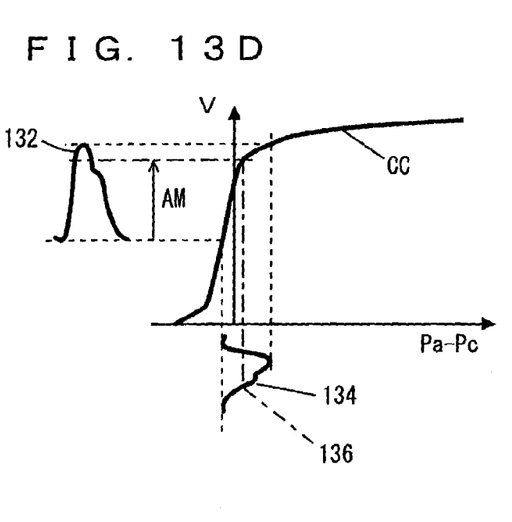

By contrast, for an elastic artery a volume pulse waveform 131 is observed as shown in FIG. 13C, and for a less elastic artery a volume pulse waveform 132 is observed as shown in FIG. 13D. Intra-arterial pressure waveforms 133 and 134 are identical, as shown in FIGS. 13C and 13D, although as arterial stiffness or PV curve is different, an observed volume pulse wave has a difference accordingly introduced. Intra-arterial pressure waveforms 133 and 134 shown have their respective average positions (positions indicating mean blood pressure) 135 and 136, which are projected, as shown in the figure, in the volume pulse waveform at a position of AM. In other words, for a less elastic artery a true average position is projected at a higher position of a pulse waveform observed.

For the above reason, pulse waveform gradient $\Delta Amr$ is used to determine a correction factor $\alpha$ in accordance with the following equation (3)

$$\alpha = A \cdot \exp\left(\frac{\Delta A_{mr}}{B}\right) \quad (3)$$

wherein constants A and B are determined for example from critical data optimally.

Then, systolic blood pressure calculator 21 employs estimated mean arterial pressure EMAP, diastolic blood pressure DBP, waveform's average value $A_{AV}$, and correction factor α and follows the following equation (4):

$$SBP = A_m \cdot \alpha \cdot \frac{EMAP - DBP}{A_{AV}} + DBP \quad (4)$$

to calculate systolic blood pressure SBP (ST9).

Systolic blood pressure SBP can be calculated for any pulse wave detected at a cuff pressure lower than estimated mean arterial pressure EMAP.

Subsequently, a blood pressure variation range as will be described later is calculated (ST10) and blood pressure display unit 22 displays a resultant measurement (ST11).

In the above described embodiment, systolic blood pressure SBP is calculated for all pulse waves detected, and their calculated systolic blood pressures SBPs are averaged together to provide a resultant measurement (a final systolic blood pressure SBP). Alternatively, an average of systolic blood pressure SBP may be calculated for each class depending on a cuff pressure at which a pulse wave is generated and such calculated values may be weighted and averaged together. In this example, a measurement proceeds, as diagrammatically shown in FIG. 14. A further reliable measurement can be obtained.

Figure 14:
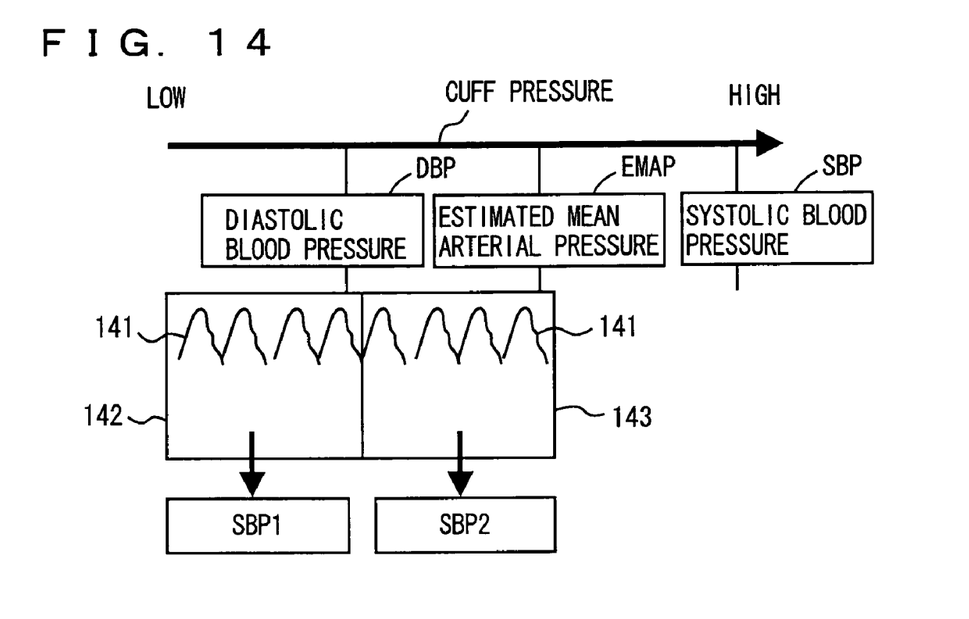
FIG. 14 is a diagram for illustrating the present invention in another embodiment.

In FIG. 14, systolic blood pressure based on a result of a measurement using a plurality of pulse waves 141 generated in classes 142 and 143, respectively, depending on cuff pressure allowing pulse wave 141 to be generated, is calculated by the following equation:

$$SBP=(K1 \cdot SBP1+K2 \cdot SBP2)/(K1+K2) \quad (5).$$

By expression (5), the classes' systolic blood pressures SBP1 and SBP2 are weighted and averaged together by predetermined constants, variables K1 and K2.

Furthermore the classes' systolic blood pressures maximum and minimum values, or standard deviation "σ" or "2×σ" or other similar value indicative of dispersion may be calculated and determined by a blood pressure variation range determiner (not shown) as a blood pressure variation range which may in turn be output for display. The user can be informed of respiratory blood pressure variation, variation attributed to arrhythmia, and the like.

Figure 15A:
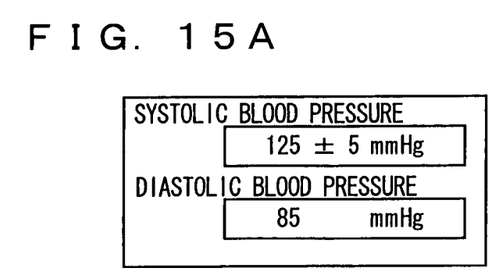
FIGS. 15A–15C show by way of example an indication to a display unit of the electronic blood pressure monitor.
Figure 15B:
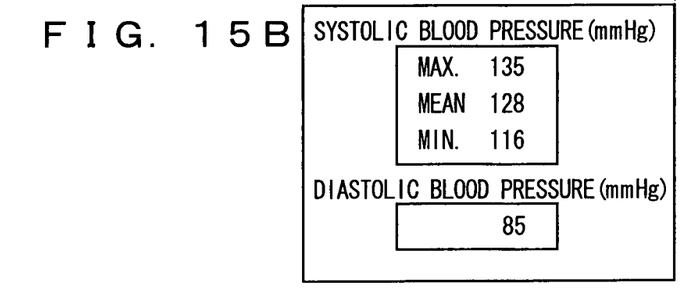
Figure 15C:
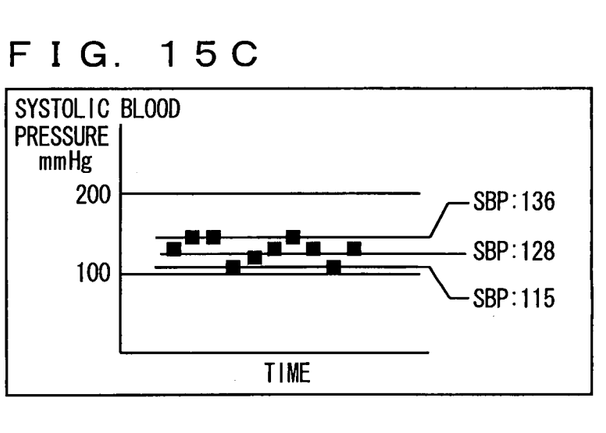

FIGS. 15A–15C show by way of example an indication of a result of a measurement to blood pressure display unit 22. Systolic blood pressure SBP and diastolic blood pressure DBP may be displayed such that systolic blood pressure SBP is accompanied by a variation range output from the blood pressure variation range determiner (see FIG. 15A). Alternatively, systolic blood pressure SBP may be displayed with a maximum, an average and a minimum individually indicated (see FIG. 15B) or it is displayed in a graph (see FIG. 15C), or the three manners of indication may all be introduced so that one of them can be selected.

It should be understood that the embodiment disclosed hereinabove is by way of illustration and example only and is not to be taken by way of limitation, the spirit and scope of the present invention being limited only by the terms of the appended claims, rather than the above description, and intended to encompass any modifications falling within the meaning and range equivalent to that of the claims.

INDUSTRIAL APPLICABILITY

The present invention is effectively applicable to an electronic blood pressure monitor that occludes a site to measured to detect a pulse wave which is in turn used to perform an operation to measure blood pressure.

The invention claimed is:

1. An electronic blood pressure monitor, comprising:
   a cuff adapted for attachment to a subject and pressurized and depressurized to measure said subject's blood pressure;
   a pulse wave detector detecting said subject's pulse wave as said cuff occludes said subject and comprising a waveform parameter calculator calculating a waveform parameter indicative of a feature of a waveform of a pulse wave detected;
   a mean blood pressure estimator estimating said subject's estimated mean blood pressure from said pulse wave detected by said pulse wave detector;
   a diastolic blood pressure detector detecting said subject's diastolic blood pressure comprising a diastolic blood pressure calculator using said waveform parameter to calculate diastolic blood pressure; and
   a systolic blood pressure calculator calculating said subject's systolic blood pressure from said estimated mean arterial pressure, said detected diastolic blood pressure and a waveform of said pulse; and
   a waveform distortion corrector correcting said waveform parameter to cancel an error introduced by a distortion of a detected pulse wave relative to said intra-arterial waveform into systolic blood pressure calculated,
   wherein said mean blood pressure estimator employs said waveform parameter to determine a reference pressure point within any range from a point of no more than systolic blood pressure to a point no less than a diastolic blood pressure and with reference to said reference pressure point calculates the estimated mean arterial pressure by using said waveform parameter correlated with an average value of an intra-arterial pressure waveform; and
   said systolic blood pressure calculator correlates said diastolic blood pressure and said estimated mean arterial pressure to said pulse waveform's maximum and average values and calculates a blood pressure corresponding to said pulse waveform's maximum value point to determine systolic blood pressure.

2. The electronic blood pressure monitor of claim 1, wherein the waveform distortion corrector employs an arterial elasticity parameter to correct for distortion.

3. The electronic blood pressure monitor of claim 1, wherein said waveform distortion corrector makes a correction based on a waveform parameter representative of a relationship between intra-arterial pressure and vascular volume obtained when said cuff effects occlusion.

4. The electronic blood pressure monitor of claim 1 or 3, wherein said mean blood pressure estimator determines as said estimated mean arterial pressure a cuff pressure allowing a pulse wave amplitude to be maximized.

5. The electronic blood pressure monitor of claim 1 or 3, wherein said mean blood pressure estimator uses an area of an apical portion of a pulse wave amplitude envelope to perform an operation to determine said estimated mean arterial pressure.

6. The electronic blood pressure monitor of claim 1 or 3, wherein said mean blood pressure estimator uses a waveform parameter indicative of stiffness in a vicinity of a pulse wave rising point to determine said estimated mean arterial pressure.

7. The electronic blood pressure monitor of claim 1 or 3, further comprising a flat-amplitude detector detecting whether there exists a cuff pressure range free of significant variation in pulse wave amplitude when said cuff pressure is changed, wherein:

when said flat amplitude detector detects that in a cuff pressure range free of significant variation in pulse wave amplitude there exists an estimated mean arterial pressure corresponding to a maximized pulse wave amplitude, the electronic blood pressure monitor proceeds to determine the systolic blood pressure from one or both of the estimated mean arterial pressures obtained by an operation based on an area of an apical portion of said pulse wave amplitude envelope and the estimated mean arterial pressure obtained as based on a waveform parameter indicative of stiffness in a vicinity of a pulse wave rising point.

8. The electronic blood pressure monitor of claim 1 or 3, wherein said systolic blood pressure calculator calculates systolic blood pressure for each pulse wave of a plurality of pulses obtained during measurement and provides an average of such obtained systolic blood pressures as an ultimate systolic blood pressure.

9. The electronic blood pressure monitor of claim 1 or 3, further comprising a pulse wave average calculator calculating average values of a plurality of pulse waves, respectively, detected by said pulse wave detector, wherein said systolic blood pressure calculator calculates systolic blood pressures for said plurality of pulse waves, respectively, from said average values calculated by said pulse wave average calculator, and determines an average of these calculated systolic blood pressures as an ultimate systolic blood pressure.

10. The electronic blood pressure monitor of claim 1 or 3, wherein said systolic blood pressure calculator calculates a systolic blood pressure for each pulse waveform of a plurality of pulses obtained during measurement, classifies such results into a plurality of classes within a range of a cuff pressure being applied when a pulse wave is generated, and performs an operation weighting an average value of each class to determine a systolic blood pressure to be a result of the measurement.

11. The electronic blood pressure monitor of claim 1 or 3, further comprising a blood pressure variation range display calculating a systolic blood pressure for each pulse wave of a plurality of pulses obtained during measurement, and displaying how a plurality of systolic blood pressures vary in value.

12. A method of measuring blood pressure employing an electronic blood pressure monitor, comprising:

providing a cuff attached to a subject and pressurizing and depressurizing the cuff in order to measure the subject's blood pressure;

detecting a pulse wave of the subject occluded by said cuff;

calculating a wave form parameter indicative of a feature of a waveform of a pulse wave detected;

estimating the subject's estimated mean blood pressure from a pulse wave detected;

using said waveform parameter to calculate the subject's diastolic blood pressure;

correcting said waveform parameter to cancel an error introduced by a distortion of a detected pulse wave relative to said intra-arterial waveform into systolic blood pressure calculate; and calculating the subject's systolic blood pressure from the estimated mean arterial pressure, the detected diastolic blood pressure and the detected pulse wave's waveform, wherein the estimating of mean blood pressure employs said waveform parameter to determine a reference pressure point within any range from a point of no more than systolic blood pressure to a point no less than a diastolic blood pressure and with reference to said reference pressure point calculates the estimated mean arterial pressure by using said waveform parameter correlated with an average value of an intra-arterial pressure waveform; and the calculating of systolic blood pressure correlates said diastolic blood pressure and said estimated mean arterial pressure to said pulse waveform's maximum and average values and calculates a blood pressure corresponding to said pulse waveform's maximum value point to determine systolic blood pressure.

* * * * *